(12) United States Patent
Perez Diaz

(10) Patent No.: US 11,602,573 B2
(45) Date of Patent: Mar. 14, 2023

(54) CLEANING SYSTEM BY MEANS OF ARTIFICIAL MIST

(71) Applicant: Universidad de Alcala, Madrid (ES)

(72) Inventor: Jose Luis Perez Diaz, Madrid (ES)

(73) Assignee: UNIVERSIDAD DE ALCALA, Madrid (ES)

( * ) Notice: Subject to any disclaimer, the term of this patent is extended or adjusted under 35 U.S.C. 154(b) by 350 days.

(21) Appl. No.: 15/799,545

(22) Filed: Oct. 31, 2017

(65) Prior Publication Data
US 2019/0117808 A1 Apr. 25, 2019

(30) Foreign Application Priority Data
Oct. 23, 2017 (ES) ................................ ES201731246

(51) Int. Cl.
| | |
|---|---|
| *A61L 2/20* | (2006.01) |
| *A61M 11/04* | (2006.01) |
| *A61L 2/02* | (2006.01) |
| *A61L 9/015* | (2006.01) |
| *B01D 47/06* | (2006.01) |

(Continued)

(52) U.S. Cl.
CPC .................................... *A61L 2/20* (2013.01); *A61L 2/02* (2013.01); *A61L 9/015* (2013.01); *A61M 11/04* (2013.01); *B01D 47/06* (2013.01); *B01D 53/18* (2013.01); *B01D 53/77* (2013.01); *B05B 7/1272* (2013.01); *B05B 7/2494* (2013.01); *B05B 7/2497* (2013.01); *B01D 2258/0283* (2013.01);

(Continued)

(58) Field of Classification Search
CPC ... A61L 2/20; A61L 9/015; A61L 2/02; B01D 53/18; B01D 53/77; B01D 47/06; B01D 2258/0283; B01D 2258/06; B01D 2259/4508; B05B 7/2497; B05B 7/1272; B05B 7/2494; B05B 7/0075; B05B 7/262; B05B 7/0416; A61M 11/04
See application file for complete search history.

(56) References Cited

U.S. PATENT DOCUMENTS

| | | | |
|---|---|---|---|
| 3,401,060 A * | 9/1968 | Watts ...................... | B05B 3/001 134/1 |
| 4,070,424 A * | 1/1978 | Olson .................... | B01D 47/06 261/142 |

(Continued)

*Primary Examiner* — Regina M Yoo
(74) *Attorney, Agent, or Firm* — Edell, Shapiro & Finnan, LLC

(57) ABSTRACT

The present invention relates to a system, and the method of application thereof, for washing and decontamination comprising nebulizing means (8) of a mixture of at least one first gas and at least one first liquid, and pressurizing means (1) of said first gas, wherein said pressurizing means (1) are in fluid communication with a first pressure-regulating valve (3) and with a second pressure-regulating valve (4),
the first pressure-regulating valve (3) being in fluid communication with a first pressurized tank (5) through first inlet means (31) of said first gas, the first pressurized tank (5) being configured to contain the first liquid, and comprising first outlet means (30) of said first liquid to the nebulizing means (8) through a first valve (6), at a first pressure that is greater than atmospheric pressure,
and wherein the second pressure-regulating valve (4) is in fluid communication with said nebulizing means (8), and is configured to pressurize the gas at a second pressure that is greater than atmospheric pressure.

17 Claims, 7 Drawing Sheets

(51) Int. Cl.
*B05B 7/24* (2006.01)
*B05B 7/12* (2006.01)
*B01D 53/77* (2006.01)
*B01D 53/18* (2006.01)
*B05B 7/00* (2006.01)

(52) U.S. Cl.
CPC .. *B01D 2258/06* (2013.01); *B01D 2259/4508* (2013.01); *B05B 7/0075* (2013.01)

(56) References Cited

U.S. PATENT DOCUMENTS

| | | | | |
|---|---|---|---|---|
| 5,881,817 | A * | 3/1999 | Mahrt | A62C 5/02 |
| | | | | 169/14 |
| 6,711,961 | B2 * | 3/2004 | Theriault | G01R 31/2849 |
| | | | | 73/865.6 |
| 7,073,734 | B2 * | 7/2006 | Dorendorf | B05B 7/0416 |
| | | | | 239/398 |
| 2019/0351370 | A1 * | 11/2019 | Fruhauf | B01D 53/56 |

* cited by examiner

CLEANING SYSTEM BY MEANS OF ARTIFICIAL MIST

FIELD OF THE INVENTION

The present invention falls within the field of cleaning and decontaminating air, or other gases or gas mixtures, of contaminants such as chemical, biological, radiological or nuclear pollutants. It can also be applied to the decontamination of surfaces or other objects.

STATE OF THE ART

Contamination consisting of small particles that float in the atmosphere is highly detrimental to the health of the population. In particular, the presence of particles having a diameter of less than 10 microns is strongly related with respiratory diseases. Heating systems and diesel engines produce particles of this size; (see, for example, Michael Allaby, "Fog, smog and Poisoned Rain", Facts on File Inc., New York, 2003). Pollen and other allergens are also classified within this range. Furthermore, the increased use of nanoparticles is a cause for concern since there is no effective solution for the filtration or elimination thereof.

It is known that natural mechanisms for removing particles from the atmosphere are dry deposition or sedimentation and sweeping. The first of these is caused by gravity simply by driving solid particles towards the ground while the last mechanism occurs when the particles act as condensation nuclei that generate water droplets, which eventually also fall to the ground. These raindrops wash other particles and droplets as they fall.

However, these natural mechanisms that depend on very particular weather conditions are often too slow for solving the daily problem in modern cities given the high rate of particle production. Thus, there is a need in the state of the art to look for systems for cleaning and decontaminating air or surfaces.

Patent application EP17382293.3 filed on 22 May 2017, describes a method for cleaning and decontaminating the air based on spraying mist with devices such as those described in application EP17382233.9 dated 28 Apr. 2017. Said device produces a jet of mist from the supply of a liquid, preferably water or an aqueous solution, and air, both above atmospheric pressure. Additionally, it has an inlet of a third component, preferably liquid, also under pressure, for the simultaneous dispersion thereof in order to favor the solubility and/or the decomposition of the pollutants. Non-exclusive examples of the third component are hydrogen peroxide for biological disinfection or nano-structured $TiO_2$ microparticles for catalysis and/or adsorption of chemical agents. The advantage of the use of mists made up of micrometric-sized droplets as described in EP17382293.3 comes from the greater efficiency of these droplets in capturing polluting particles with respect to other sized droplets when falling due to gravity, in addition to the fact that both the amount of liquid used and the amount of waste generated, are minimized.

Although this system provides satisfactory results, it is still necessary to provide alternative or improved cleaning and decontaminating systems, making a more efficient use of resources.

SUMMARY OF THE INVENTION

Figure 1:
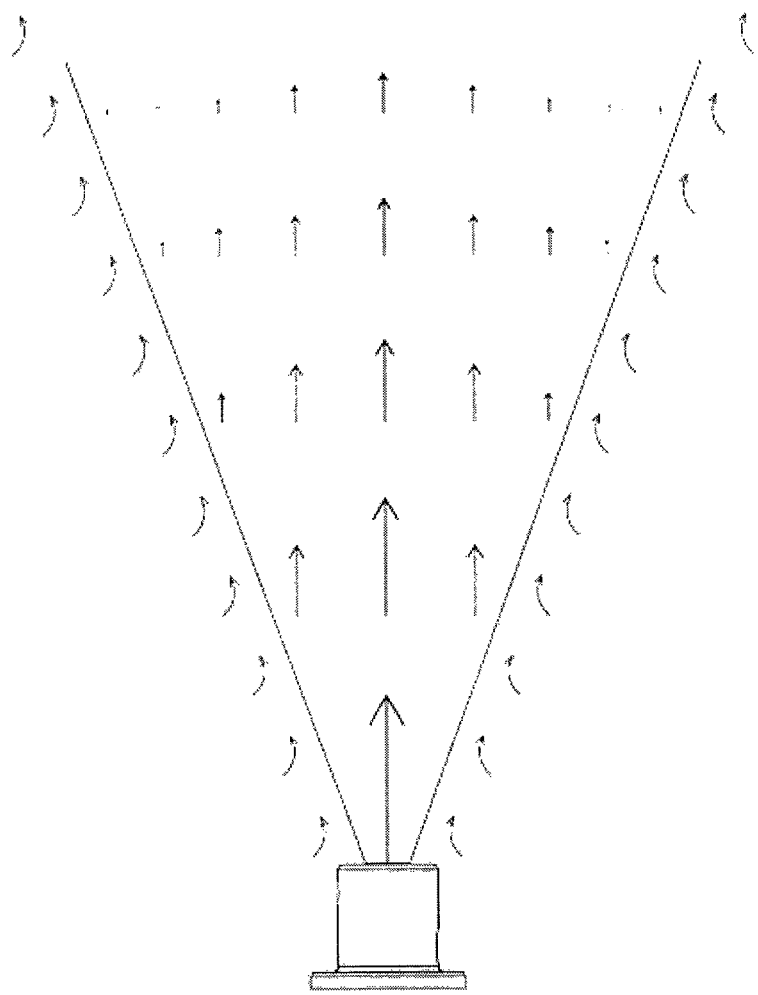
FIG. 1 is a schematic representation of the Venturi effect.
Figure 2:
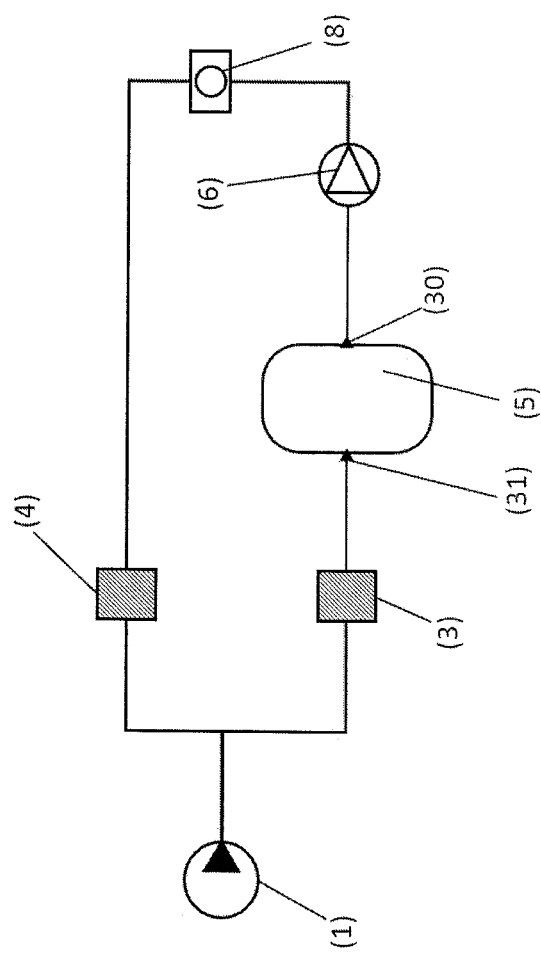
FIG. 2 describes a system according to the present invention.
Figure 3:
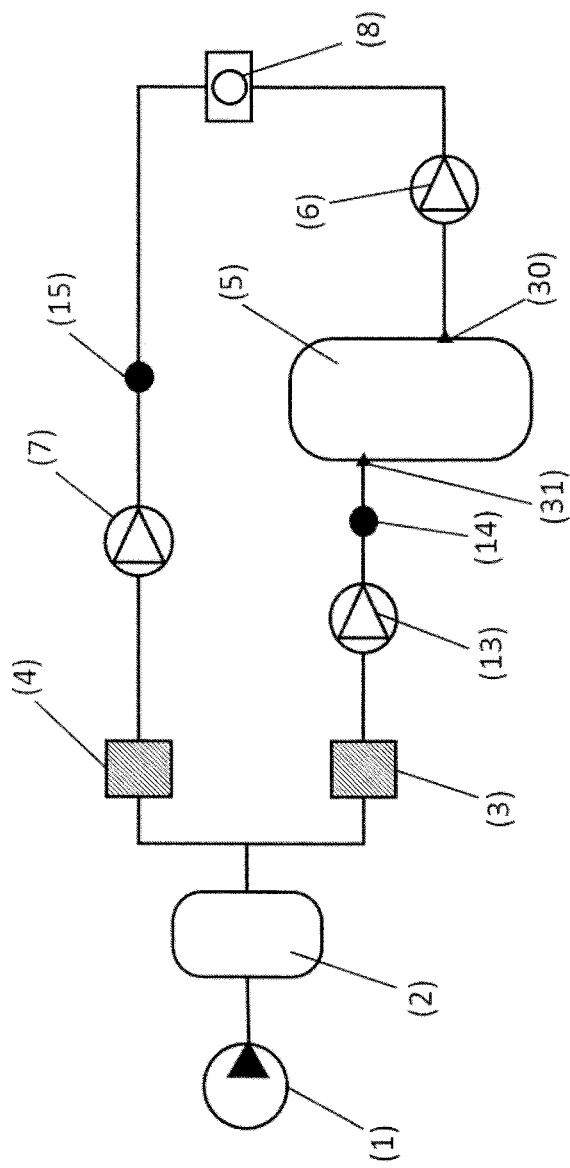
FIG. 3 describes a system according to the present invention according to one of the embodiments thereof including gas accumulating means (2) for the first gas.

Thus, the inventor of the present application is working on the decontamination of air and other gases by means of the use of nebulizers. To this end, mist is created by means of mixtures of liquids and gases that are expelled at high pressures, thus creating mist with approximately micrometric sized droplets. In the search for more and more efficient systems, the researcher has found that it is not only important to provide adequate-sized droplets, and therefore a total pressure at which the appropriate mixture is expelled, but it is also essential that the relative pressure between the gaseous and liquid components be maintained stable during the operation time of the system. The researcher has discovered that small variations in the relative pressures of the different components can significantly affect that size distribution and the amount of droplets generated, and also fundamentally, the speed of the jet, which produces changes in the efficiency of cleaning and decontaminating. The researcher has discovered that maintaining stability in the pressures and, even more so, stability in the relationship between the pressures of the liquid and gaseous components is essential.

Thus, a first aspect of the invention (see FIG. 2) is a washing and decontaminating system comprising nebulizing means (8) of a mixture of at least one first gas and at least one first liquid, and pressurizing means (1) of said first gas, wherein said pressurizing means (1) are in fluid communication with a first pressure-regulating valve (3) and with a second pressure-regulating valve (4), the first pressure-regulating valve (3) being in fluid communication with a first pressurized tank (5) through first inlet means (31) of said first gas, the first pressurized tank (5) being configured to contain the first liquid, and comprising first outlet means (30) of said first liquid to the nebulizing means (8) through a first valve (6), at a first pressure that is greater than atmospheric pressure, and wherein the second pressure-regulating valve (4) is in fluid communication with said nebulizing means (8), and is configured to pressurize the gas at a second pressure that is greater than atmospheric pressure.

In this way, the same gas (or mixture of gases), preferably air, serves on the one hand to directly feed the nebulizing means (8), and at the same time, the first liquid (or other liquids), the pressure being controlled independently in each case.

A second aspect of the invention is therefore a method for washing and decontaminating which comprises pressurizing a first gas by means of pressurizing means (1), which are in fluid communication with a first pressure-regulating valve (3) and with a second pressure-regulating valve (4), such that the first pressure-regulating valve (3) regulates the pressure of the first gas in a first pressurized tank (5) configured to contain a first liquid and comprising first outlet means (30) and first inlet means (31), such that said first liquid is in turn in fluid communication with nebulizing means (8) through a first valve (6), the first liquid being at a first pressure that is greater than atmospheric pressure, and wherein the second pressure-regulating valve (4) regulates the pressure at which the first gas is fed to said nebulizing means (8), said first gas being at a second pressure that is greater than atmospheric pressure.

In this way, the regulation of the first pressure and the second pressure can be carried out independently by the first pressure-regulating valve (3) and by the second pressure-regulating valve (4), respectively. The pressure at which the first liquid and the first gas are fed to the nebulizing means (8) can be controlled precisely and independently, and they remain constant during the operation of the system.

The system and the method of the invention enable the efficiency of the decontamination to be improved by keeping the relative pressure of the components of the mixture propelled by the nozzle constant, since the use of the first pressure-regulating valve (3) and the second pressure-regulating valve (4) enables the adjustment of different pressures for each component of the nebulizer mixture.

Without serving as a limitation to the invention, the authors believe that propelling mist under pressure through a nozzle produces a beneficial effect that multiplies the effectiveness of the micrometric droplets in their function of cleaning through collision and entrapment of polluting particles by forming a cone that interacts with the surrounding air, suctioning it through the effect of speed (also called the Venturi effect) while at the same time producing a high velocity gradient at the edges and thus facilitating the collision of mist droplets with the particles that are cleaned from the air. The authors believe that the jet also generates turbulences and fluid dynamic instabilities such as Kelvin-Helmholtz instability. Both effects of the jet edge increase the effective cross-section of the liquid droplets in their collision action, as well as the collision rate, making the cleaning action of the jet edge even greater than that of mist deposition due to gravity. Thus, the importance of keeping the relative pressure of the various components of the mixture stable has been surprising, especially when compared to a system that uses pumps to feed some of the components of the mixture. Therefore, the system of the invention also reduces the number of mechanic or propulsion elements to one or a plurality of gas compressors, without the need for pumps.

The system of the invention enables the stability of the supply of the gases and liquids used for generating the mist. In addition, it allows different pressures for each component to be independently selected, thus being able to adapt the size of the droplets in the mist and the quantity thereof. This provides the system of the invention with enormous flexibility for adapting the characteristics of the generated mist to different pollutants and situations. It also allows the storage of liquids or components for generating mist such that it is easier to control or prevent the spread of Legionelosis or other microorganisms. Another advantage of the invention is that it enables a portable assembly to be created and it is capable of being boarded on vehicles that can be moved to the site of the contamination. It also offers greater reliability by avoiding the use of a mechanical element prone to breakdowns, such as a pumping system.

DETAILED DESCRIPTION OF THE INVENTION

The present invention considers that the term "liquid" encompasses liquids the components of which are completely dissolved, but also liquids with only partially dissolved solutes as well as suspensions.

For reasons of economy, in all the embodiments of the present invention, it is preferable that the compressed gas be air.

The notations "first", "second", third", "fourth", "fifth", etc. are used throughout this document to refer to some of the elements of the invention. For example, reference is made to a "first valve", a "second valve", etc. This notation does not imply any order or prevalence and is used exclusively to unequivocally label an element, and thus distinguish it from other similar elements. This notation, as described below in the different embodiments and examples, enables there to be different combinations of similar elements, regardless of the nomenclature used. For example, one embodiment may include a first valve and a third valve without the need to have a second valve in said embodiment.

The present invention is described below making reference to the figures of the invention by means of examples of specific non-limiting embodiments.

According to an embodiment (see FIG. 3), the system of the invention comprises one or a plurality of compressors (1) that supply a first compressed gas, preferably compressed air, to gas accumulation means (2), which in turn supplies the compressed gas in a stable manner to a first pressure-regulating valve (3) and to a second pressure-regulating valve (4). Said first pressure-regulating valve (3) supplies the compressed gas to a first pressurized tank (5), preferably through the upper part thereof. The pressurized liquid is expelled from the first pressurized tank (5) towards the nebulizing means (8) through the first valve (6). The second pressure-regulating valve (4), according to the present invention, is in fluid communication with said nebulizing means (8), preferably through a third valve located in series with said second pressure-regulating valve (4), and is configured to pressurize the gas at a second pressure that is greater than atmospheric pressure. A second valve (13) is located between the first pressure-regulating valve (3) and the first pressurized tank (5), which enables the passage of the first gas, as well as first non-return means (14), to be opened and closed. Thus, closing the first valve (6) and the second valve (13) enables isolating the first pressurized tank during the feeding of the first liquid. Similarly, a third valve (7) is located between the second pressure-regulating valve (4) and the nebulizing means (8), which enables the passage of the first gas, as well as second non-return means (15), to be opened and closed.

The compression means (1) may encompass one or more compressors according to any of the embodiments of the invention. It is a design characteristic that the person skilled in the art can adjust according to the characteristics of the available compressors and the needs of the system (power, size, etc.).

The first pressurized tank (5) is preferably characterized for having feeding means of the first liquid such that the air supplied by the first pressure-regulating valve (3) enters through the upper part of said tank and pushes the first liquid making it flow towards the nebulizing means (8). Thus, it is preferable that, in any of the embodiments of the present invention, the first inlet means (31) of the first gas be located in the first pressurized tank (5) at a height that is higher than the first outlet means (30).

Said nebulizing means are preferably of the type described in European application EP17382233.9, the contents of which are included in their entirety as a reference. Therefore, preferably, said nozzle combines two or more substances introduced through at least a first inlet and a second inlet and sprays the resulting atomized droplets through an outlet, capable of optimizing the flow rate and the size of the droplets through a modular design based on exchangeable disc-shaped modules. When they are stacked in a hollow cylindrical casing made up of a first casing and a second casing, the plurality of modules make up a first mixing chamber and a second mixing chamber connected through a spiral module. Furthermore, when said stacking occurs, the first inlet is connected to the first mixing chamber, the outlet is connected to the second mixing chamber, and the second outlet may be connected to the first mixing chamber or to the second mixing chamber depending on the configuration selected by the user.

Figure 6:
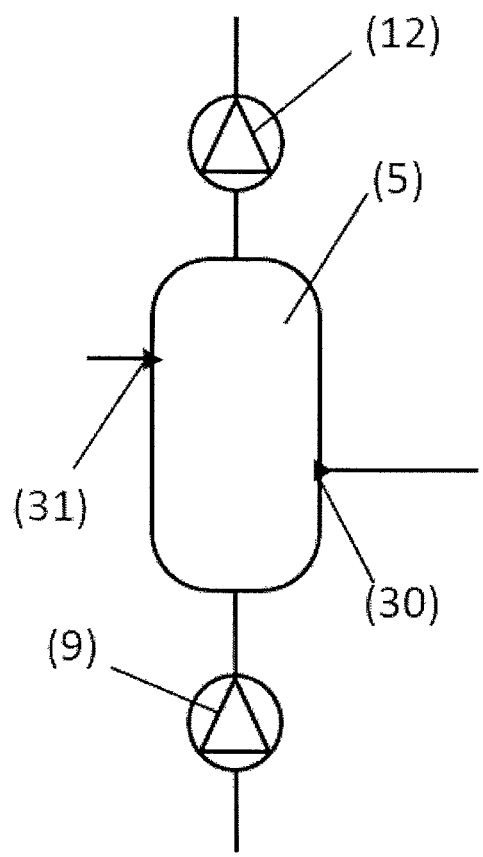
FIG. 6 is a detailed view of the first pressurized tank (5) according to one of the embodiments of the invention.

With reference to FIG. 6, it is preferable that the feeding means comprise a first feed valve (9) and a first evacuation valve (12). Preferably, said first feed valve (9) is connected to the lower part of the first pressurized tank. This configuration makes it possible to fill the first pressurized tank (5) by opening the supply of the first liquid, for example, by using a pump (10) from a tank of the first liquid (11), or alternatively, from a supply line of the first liquid, such as, for example, a drinking water hose from a sanitary water network (not shown in the figure). Opening the evacuation valve (12), preferably connected to the upper part of the first pressurized tank (5), allows outlet of the gas during filling, thus relaxing the pressure necessary for the supply of the first liquid. In an advantageous embodiment, the system is provided with a second valve (13) located between the first pressure-regulating valve (3) and the first pressurized tank (5). Closing this second valve (13) allows the first pressurized tank (5) to be made independent during the filling process. Once the filling is complete, the first feed valve (9) and the first evacuation valve (12) are closed, while the second valve (13) is opened, thus pressurizing the first pressurized tank (5) and leaving it ready for actuation by opening the first valve (6).

Preferably, any of the embodiments of the invention comprise first non-return means (14) in series with the first pressure-regulating valve (3), preferably at the outlet of the second valve (13), and/or second non-return means (15) in series with the second pressure-regulating valve (4), preferably at the outlet of the third valve (7). These non-return devices prevent backflow from occurring at all times, this being especially important during system connection and disconnection, when there may be liquid pressure but not air pressure.

Preferably, the system can also be provided with elements that facilitate the actuation and control thereof. Thus, for example, the system of the invention may comprise first remote actuation means (18) in series with the first pressure-regulating valve (3), and/or second remote actuation means (16) in series with the second pressure-regulating valve (4), this actuation being, for example, but not exclusively, electric. Moreover, the system of the invention may comprise first means for measuring the flow rate (19), in series with the first pressure-regulating valve (3), and second means for measuring the flow rate (17), in series with the second pressure-regulating valve (4). In this way, by keeping the first valve (6) and/or the third valve (7) open, the system will activate when opening the first remote actuation means (18) and the second remote actuation means (16). The first remote actuation means (18) and the second remote actuation means (16) may be individual units, for example, solenoid valves, or they may be integrated with the first pressure-regulating valve (3) and the second pressure-regulating valve (4), respectively.

Figure 4:
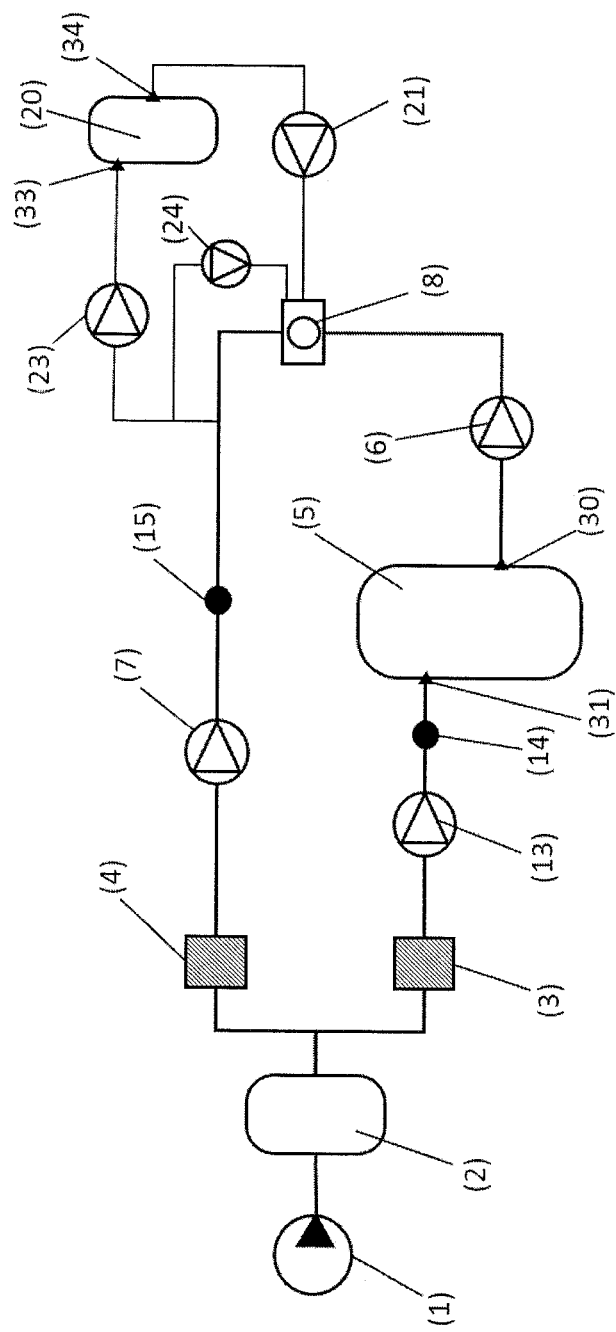
FIG. 4 describes a system according to the present invention according to one of the embodiments thereof including the use of a second liquid.

The system of the invention can therefore provide at least one gas and at least one liquid to the nebulizing means (8). By way of example, a system according to the present invention is described below, in which the nebulizing mixture also includes a second liquid (see FIG. 4). According to this embodiment, the system includes a third pressure-regulating valve (23) in fluid communication with the second pressure-regulating valve (4). The third pressure-regulating valve (23) is in fluid communication with a second pressurized tank (20) through second inlet means (33) of said first gas, the second pressurized tank (20) being configured to contain a second liquid, and comprising second outlet means (34) of said second liquid towards the nebulizing means (8), through a fourth valve (21), at a third pressure that is higher than atmospheric pressure. In this configuration, the system may comprise a fifth valve (24) that enables the flow of the first gas towards the nebulizing means (8) to be selectively interrupted. Alternatively, the second pressurized tank (20) may have filling means that enable it to be filled with the second liquid, which may be a suspension. Said second pressurized tank (20) may comprise second feeding means of the second liquid, which provide the second liquid, while the third pressure-regulating valve (23) interrupts the passage of the pressurized gas when it is closed.

Given that on occasions the second liquid must be applied only for a short time and in relatively small quantities, for example, if it contains substances having catalytic properties, the second pressurized tank (20) may be sufficiently small so that, together with the nebulizing means (8), and the valves (21), (23) and (24), they can make up an assembly capable of being transported by a man or a crane, provided that the pipes supplying the second liquid and the compressed gas are flexible. Said configuration may even comprise the first valve (6), provided that the means for supplying the first liquid from the first pressurized tank (5) are flexible.

Another embodiment of the present invention is described with reference to FIG. 5. According to this embodiment, the system comprises pressurizing means (1) of the first gas, which are in fluid communication with the gas accumulation means (2), from where the first gas is distributed at stable pressure to the first pressure-regulating valve (3) and to the second pressure-regulating valve (4), the first pressure-regulating valve (3) being in fluid communication with a first pressurized tank (5) through first inlet means (31) of said first gas, the first pressurized tank (5) being configured for containing the first liquid, and comprising first outlet means (30) of said first liquid towards the nebulizing means (8) through a first valve (6), at a first pressure that is higher than atmospheric pressure. According to this embodiment, a second valve (13) and first non-return means (14) are placed between the first pressure-regulating valve (3) and the first pressurized tank (5). Moreover, the first remote actuation means (18), as well as first means for measuring the flow rate (19), are located between the first valve (6) and the first pressurized tank (5). The first inlet means (31) of said first gas are located at a height that is higher than the first outlet means (30).

Figure 5:
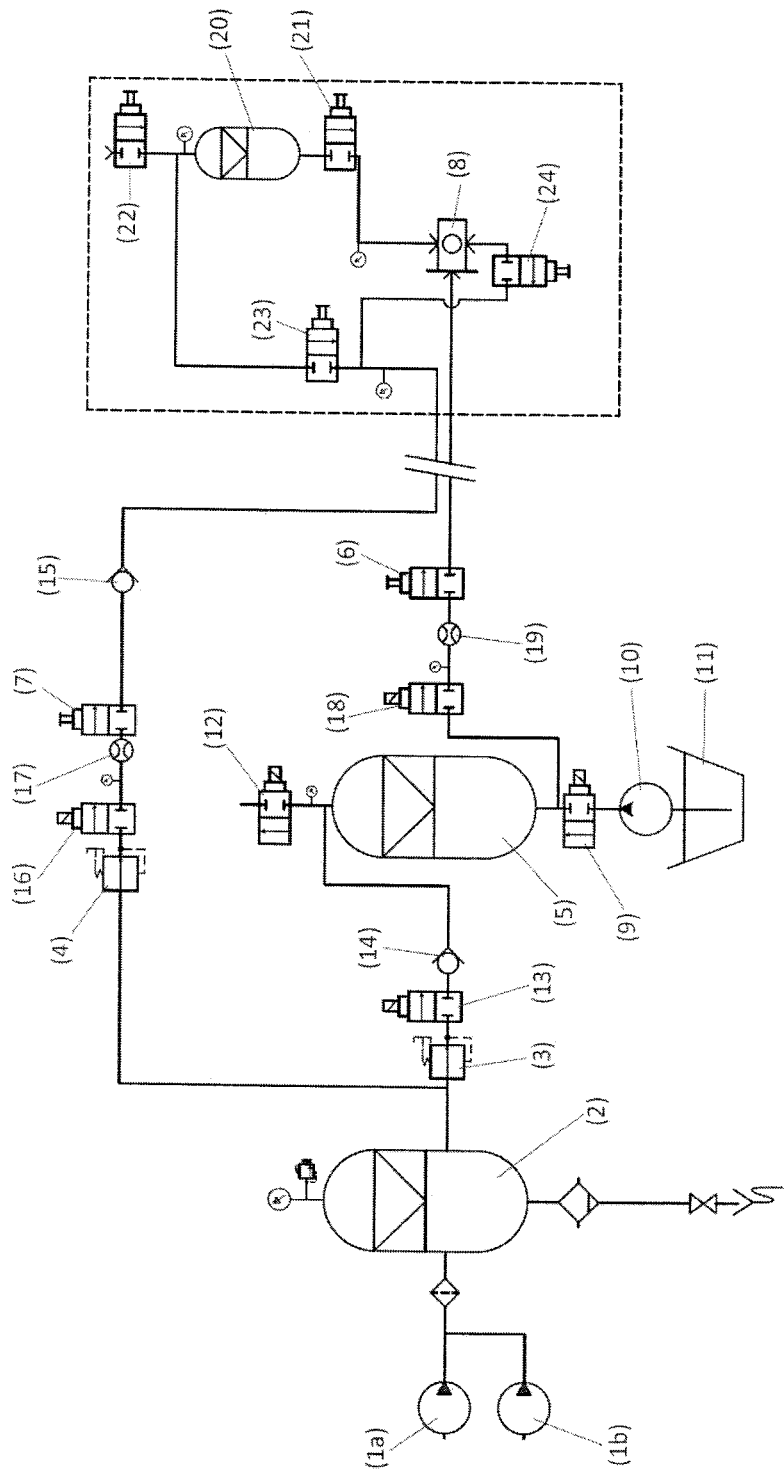
FIG. 5 describes a system according to the present invention according to one of the embodiments thereof including several optional systems.

Furthermore, as shown in FIG. 5, the compressed gas line comprises similar equipment. Thus, in line with the second pressure-regulating valve (4), second remote actuation means (16), second means for measuring the flow rate (17) and a third valve (7) are located such that the pressure of the gas fed to the nebulizing means (8) is a second pressure that is higher than atmospheric pressure. Second non-return means (15) are located at the outlet of the third valve (7).

The embodiment shown in FIG. 5 also shows a circuit for feeding a second liquid to the nebulizing means (8), including a third pressure-regulating valve (23) in fluid communication with the second pressure-regulating valve (4). The third pressure-regulating valve (23) is also in fluid communication with a second pressurized tank (20) through second inlet means (33) of said first gas, the second pressurized tank (20) being configured to contain a second liquid, and comprising second outlet means (34) of said second liquid towards the nebulizing means (8), through a fourth valve (21), at a third pressure that is higher than atmospheric pressure. In this configuration, the system may comprise a fifth valve (24) that enables the flow of the first gas towards the nebulizing means (8) to be selectively interrupted. Alternatively, the second pressurized tank (20) may have filling means that enable it to be filled with the second liquid, which may be a suspension. Said second pressurized tank (20) may comprise second feeding means of the second liquid, which provide the second liquid, while the third pressure-regulating valve (23) interrupts the passage of the pressurized gas when it is closed.

Note that regardless of the number of gases and liquids for which it is configured, the system of the invention allows one or more of these elements of the mixture to be blocked as long as at least one gas and at least one liquid are fed to the nebulizing means (8). For example, in the event that the system is configured to provide a first liquid, a second liquid and a first gas (for example the systems described in FIG. 4 or 5) it is possible to block the supply of the second liquid so that the mixture fed to the nebulizing means (8) is exclusively comprised of the first liquid and the first gas.

The inlet and outlet means in the present invention are preferably openings in the corresponding tank.

APPLICATIONS

As mentioned above, the present invention describes a system for washing and decontaminating air, gases, ducts and/or surfaces by means of jets of pressurized mist. The system preferably comprises a plurality of nebulizing means (8), preferably nozzles. However, the system may also have other uses. For example, parallel connection of a plurality of nozzles can produce a mist jet barrier. Other geometries in the distribution of the nozzles can enable the air contained in an entire enclosure to be washed.

Figure 7:
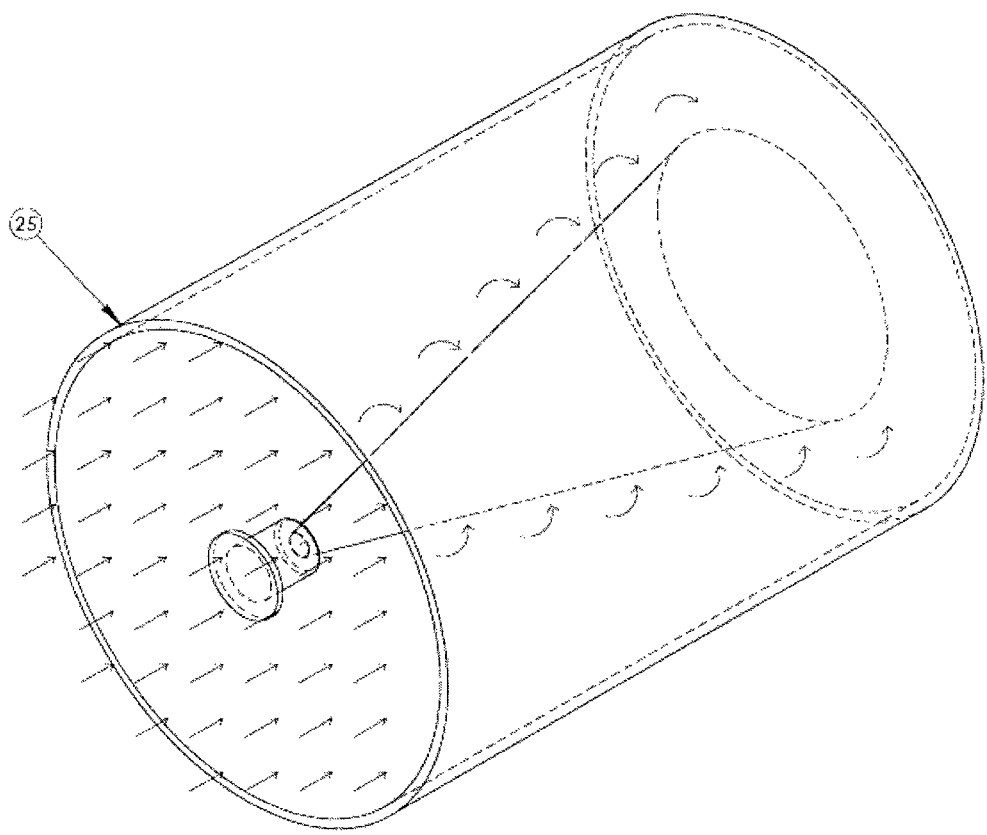
FIG. 7 is a schematic representation of the nozzle inserted in a duct thus enhancing the Venturi effect.

Another non-exclusive alternative consists in introducing the nebulizing means (8) into a wider duct (25), for example a tubular duct as shown in FIG. 7, such that, through the Venturi effect, it sucks air from the back and propels it, along with the released mist, through the duct while cleaning it. This alternative is very useful for all kinds of ventilation ducts, for example, for a clean air supply or gas scrubbing system characterized by a nozzle that provides a jet of pressurized mist in a duct in the direction of forward flow.

In a non-exclusive alternative configuration, the system has a wall, preferably vertical, and at a certain distance from the nozzle, for collecting waste through the impact of the jet against the same.

In short, the system of the invention enables the cleaning of air indoors, outdoors, in ventilation or gas ducts, chimneys etc. with a small amount of liquid.

CLAUSES

CLAUSE 1: A washing and decontaminating system comprising nebulizing means (8) for a mixture of at least one first gas and at least one first liquid, and pressurizing means (1) of said first gas, wherein said pressurizing means (1) are in fluid communication with a first pressure-regulating valve (3) and with a second pressure-regulating valve (4), the first pressure-regulating valve (3) being in fluid communication with a first pressurized tank (5) through first inlet means (31) of said first gas, the first pressured tank (5) being configured to contain the first liquid, and comprising first outlet means (30) of said first liquid to the nebulizing means (8) through a first valve (6), at a first pressure that is higher than atmospheric pressure, and wherein the second pressure-regulating valve (4) is in fluid communication with said nebulizing means (8), and is configured to pressurize the gas at a second pressure that is greater than atmospheric pressure.

CLAUSE 2: The system according to clause 1, characterized in that said first inlet means (31) of the first gas are located in the first pressurized tank (5) at a height that is higher than the first outlet means (30).

CLAUSE 3: The system according to any one of the preceding clauses, characterized in that it comprises gas accumulation means (2) located between
the pressurizing means (1) of the first gas, and
the first pressure-regulating valve (3) and the second pressure-regulating valve (4).

CLAUSE 4: The system according to any one of the preceding clauses, characterized in that the first pressurized tank (5) comprises means for feeding said first liquid.

CLAUSE 5: The system according to any one of the preceding clauses, characterized in that it comprises a second valve (13) located between the first pressure-regulating valve (3) and the first pressurized tank (5).

CLAUSE 6: The system according to any one of the preceding clauses, characterized in that it comprises a third valve (7) located between the second pressure-regulating valve (4) and the nebulizing means (8).

CLAUSE 7: The system according to any one of the preceding clauses, characterized in that it comprises first remote actuating means (18) in series with the first pressure-regulating valve (3).

CLAUSE 8: The system according to any one of the preceding clauses, characterized in that it comprises second remote actuating means (16) in series with the second pressure-regulating valve (4).

CLAUSE 9: The system according to any one of the preceding clauses, characterized in that the first pressurized tank (5) comprises first feeding means of said first liquid.

CLAUSE 10: The system according to clause 9, characterized in that said first feeding means comprise a first feed valve (9) and a first evacuation valve (12).

CLAUSE 11: The system according to any one of the preceding clauses, characterized in that it comprises first non-return means (14) in series with the first pressure-regulating valve (3).

CLAUSE 12: The system according to any one of the preceding clauses, characterized in that it comprises second non-return means (15) in series with the second pressure-regulating valve (4).

CLAUSE 13: The system according to any one of the preceding clauses, characterized in that it comprises a third pressure-regulating valve (23) connected in series with the second pressure-regulating valve (4).

CLAUSE 14: The system according to clause 13, characterized in that the third pressure-regulating valve (23) is in fluid communication with a second pressurized tank (20) through second inlet means (33) of said first gas, the second pressurized tank (20) being configured to contain a second liquid, and comprising second outlet means (34) of said second liquid towards the nebulizing means (8), through a fourth valve (21), at a third pressure that is higher than atmospheric pressure.

CLAUSE 15: The system according to any one of clauses 13 or 14, characterized in that before the third pressure-regulating valve (23) it comprises a fifth valve (24) that enables the flow of the first gas towards the nebulizing means (8) to be selectively interrupted.

CLAUSE 16: The system according to any one of clauses 14 or 15, characterized in that the second pressurized tank (20) comprises second means for feeding the second liquid.

CLAUSE 17: The system according to any one of the preceding clauses, characterized in that it comprises first means for measuring the flow rate (19), in series with the first pressure-regulating valve (3), and second means for measuring the flow rate (17), in series with the second pressure-regulating valve (4).

CLAUSE 18: The system according to any one of the preceding clauses, characterized in that it has a pressure of between 8 bar and 20 bar.

CLAUSE 19: A method for washing and decontaminating, which comprises pressurizing a first gas by means of pressurizing means (1), which are in fluid communication with a first pressure-regulating valve (3) and with a second pressure-regulating valve (4), such that the first pressure-regulating valve (3) regulates the pressure of the first gas in a first pressurized tank (5) configured to contain a first liquid and comprising first outlet means (30) and first inlet means (31), such that said first liquid is in turn in fluid communication with nebulizing means (8) through a first valve (6), the first liquid being at a first pressure that is greater than atmospheric pressure, and wherein the second pressure-regulating valve (4) regulates the pressure at which the first gas is fed to said nebulizing means (8), said first gas being at a second pressure that is greater than atmospheric pressure.

The research work leading to this invention was partially funded by the Seventh Framework Program of the European Union under contract number 312804.

The invention claimed is:

1. A washing and decontaminating system comprising:

a nebulizer having a first inlet for receiving a first gas and a second inlet for receiving a first liquid;

a first pressure-regulating valve located downstream and in fluid communication with a pressurizing means, the first pressure-regulating valve being configured to regulate the first gas at a first pressure greater than atmospheric pressure;

a second pressure-regulating valve in fluid communication with the pressurizing means and with the first inlet of the nebulizer, the second pressure-regulating valve being configured to regulate the first gas at a second pressure greater than atmospheric pressure, the second pressure-regulating valve not being in series with the first pressure-regulating valve;

a first tank configured to store the first liquid and to be pressurized by the first gas at the first pressure, the first tank having a first inlet in fluid communication with the first pressure-regulating valve and a first outlet through which the first liquid exits the first tank, the first outlet being in fluid communication with the nebulizer;

a first valve located in a fluid pathway between the first outlet of the first tank and the second inlet of the nebulizer, the first valve configured to assume a closed position in which the first liquid is prevented from passing through the first valve and an open position in which the first liquid is able to pass through the first valve;

a second valve located between and in fluid communication with the first pressure-regulating valve and the first tank, the second valve configured to assume a closed position in which the first gas is prevented from passing through the second valve and an open position in which the first gas is able to pass through the second valve;

the washing and decontaminating system being configured such that upon the first liquid residing in the first tank and the first gas at the first pressure being delivered to the first tank, the first liquid is capable of being delivered to the nebulizer for being mixed with the first gas without the use of a pump;

the nebulizer being configured to mix the first gas delivered through the second pressure-regulating valve with the first liquid;

a first flow rate measuring device located in a flow path between the first outlet of the first tank and the second inlet of the nebulizer, the first flow rate measuring device being configured to measure a flow rate of the first liquid, and a second flow rate measuring device located between the second pressure-regulating valve and the first inlet of the nebulizer, the second flow rate measuring device being configured to measure a flow rate of the first gas.

2. The washing and decontaminating system according to claim 1, wherein the first inlet of the first tank is located at a first height and the first outlet of the first tank is located at a second height, the first height being higher than the second height.

3. The washing and decontaminating system according to claim 1, further comprising gas accumulation means located between and in fluid communication with the pressurizing means of the first gas and the first and second pressure-regulating valves when the nebulizer is in use mixing the first gas with the first liquid, the gas accumulation means configured to supply the first gas produced by the pressurizing means in a stable manner to the first and second pressure-regulating valves.

4. The washing and decontaminating system according to claim 1, wherein the first tank includes a second inlet through which the first liquid is introduced into the first tank.

5. The washing and decontaminating system according to claim 4, further comprising a first feed valve in fluid communication with the second inlet of the first tank and a first evacuation valve in fluid communication with a second outlet of the first tank.

6. The washing and decontaminating system according to claim 1, further comprising a third valve located between the second pressure-regulating valve and the nebulizer, the third valve configured to assume a closed position in which the first gas is prevented from passing through the third valve and an open position in which the first gas is able to pass through the third valve.

7. The washing and decontaminating system according to claim 1, further comprising a second remote actuation means in series with the second pressure-regulating valve.

8. The washing and decontaminating system according to claim 1, further comprising a first non-return device in series with the first pressure-regulating valve, the first non-return device being configured to prevent at all times backflow of the first liquid towards the pressurizing means of the first gas.

9. The washing and decontaminating system according to claim 1, further comprising a second non-return device in series with the second pressure-regulating valve, the second non-return device being configured to prevent at all times backflow of the first liquid towards the pressurizing means of the first gas.

10. The washing and decontaminating system according to claim 1, further comprising a third pressure-regulating valve connected in series with the second pressure-regulating valve, the third pressure-regulating valve configured to regulate the first gas at a third pressure that is greater than atmospheric pressure.

11. The washing and decontaminating system according to claim 10, further comprising a second tank configured to store a second liquid, the second tank having a first inlet in fluid communication with the third pressure-regulating valve and a first outlet through which the second liquid exits the second tank, the first outlet of the second tank being in fluid communication with a third inlet of the nebulizer, the washing and decontaminating system further comprising a fourth valve located in a fluid pathway between the first outlet of the second tank and the third inlet of the nebulizer.

12. The washing and decontaminating system according to claim 11, wherein the second tank includes a second inlet through which the second liquid is introduced into the second tank.

13. The washing and decontaminating system according to claim 10, further comprising a fifth valve located upstream the third pressure-regulating valve that enables the flow of the first gas towards the nebulizer to be selectively interrupted.

14. A washing and decontaminating system comprising:
a nebulizer having a first inlet for receiving a first gas and a second inlet for receiving a first liquid;
a first pressure-regulating valve located downstream and in fluid communication with a pressurizing means, the first pressure-regulating valve being configured to regulate the first gas at a first pressure;
a second pressure-regulating valve in fluid communication with the pressurizing means and with the first inlet of the nebulizer, the second pressure-regulating valve being configured to regulate the first gas at a second pressure, the second pressure-regulating valve not being in series with the first pressure-regulating valve;
a third pressure-regulating valve connected in series with the second pressure-regulating valve, the third pressure-regulating valve configured to regulate the first gas at a third pressure that is greater than atmospheric pressure;
a first tank configured to store the first liquid and to be pressurized by the first gas at the first pressure, the first tank having a first inlet in fluid communication with the first pressure-regulating valve and a first outlet through which the first liquid exits the first tank, the first outlet being in fluid communication with the nebulizer;
a second tank configured to store a second liquid, the second tank having a first inlet in fluid communication with the third pressure-regulating valve and a first outlet through which the second liquid exits the second tank, the first outlet of the second tank being in fluid communication with a third inlet of the nebulizer, the washing and decontaminating system further comprising a fourth valve located in a fluid pathway between the first outlet of the second tank and the third inlet of the nebulizer; and
a first valve located in a fluid pathway between the first outlet of the first tank and the second inlet of the nebulizer, the first valve configured to assume a closed position in which the first liquid is prevented from passing through the first valve and an open position in which the first liquid is able to pass through the first valve;
the washing and decontaminating system being configured such that upon the first liquid residing in the first tank and the first gas at the first pressure being delivered to the first tank, the first liquid is capable of being delivered to the nebulizer for being mixed with the first gas without the use of a pump;
the nebulizer being configured to mix the first gas delivered through the second pressure-regulating valve with the first liquid.

15. The washing and decontaminating system according to claim 14, further comprising a fifth valve located upstream the third pressure-regulating valve that enables the flow of the first gas towards the nebulizer to be selectively interrupted.

16. The washing and decontaminating system according to claim 14, wherein the second tank includes a second inlet through which the second liquid is introduced into the second tank.

17. A washing and decontaminating system comprising:
a nebulizer having a first inlet for receiving a first gas and a second inlet for receiving a first liquid;
a first pressure-regulating valve located downstream and in fluid communication with a pressurizing means, the first pressure-regulating valve being configured to regulate the first gas at a first pressure greater than atmospheric pressure;
a second pressure-regulating valve in fluid communication with the pressurizing means and with the first inlet of the nebulizer, the second pressure-regulating valve being configured to regulate the first gas at a second pressure greater than atmospheric pressure, the second pressure-regulating valve not being in series with the first pressure-regulating valve;
a first tank configured to store the first liquid and to be pressurized by the first gas at the first pressure, the first tank having a first inlet in fluid communication with the first pressure-regulating valve and a first outlet through which the first liquid exits the first tank, the first outlet being in fluid communication with the nebulizer;
a first valve located in a fluid pathway between the first outlet of the first tank and the second inlet of the nebulizer, the first valve configured to assume a closed position in which the first liquid is prevented from passing through the first valve and an open position in which the first liquid is able to pass through the first valve;
a second valve located between and in fluid communication with the first pressure-regulating valve and the first tank, the second valve configured to assume a closed position in which the first gas is prevented from passing through the second valve and an open position in which the first gas is able to pass through the second valve;

the washing and decontaminating system being configured such that upon the first liquid residing in the first tank and the first gas at the first pressure being delivered to the first tank, the first liquid is capable of being delivered to the nebulizer for being mixed with the first gas without the use of a pump;

the nebulizer being configured to mix the first gas delivered through the second pressure-regulating valve with the first liquid;

a third pressure-regulating valve connected in series with the second pressure-regulating valve, the third pressure-regulating valve configured to regulate the first gas at a third pressure that is greater than atmospheric pressure; and a fifth valve located upstream the third pressure-regulating valve that enables the flow of the first gas towards the nebulizer to be selectively interrupted.

\